United States Patent [19]

Steinbock

[11] Patent Number: 4,496,319
[45] Date of Patent: Jan. 29, 1985

[54] DENTAL ARTICULATOR WITH SPATIALLY ORIENTED MOUNTING TABLE

[75] Inventor: Allen F. Steinbock, Louisville, Ky.

[73] Assignee: Whip-Mix Corporation, Louisville, Ky.

[21] Appl. No.: 409,592

[22] Filed: Aug. 19, 1982

[51] Int. Cl.³ .............................................. A61C 11/00
[52] U.S. Cl. ........................................ 433/57; 433/56; 433/60
[58] Field of Search ....................... 433/55, 56, 57, 60; 33/174 D

[56] References Cited

U.S. PATENT DOCUMENTS

| | | | |
|---|---|---|---|
| 2,510,152 | 6/1950 | Stoll | 433/57 |
| 2,754,588 | 7/1956 | Cordell | 433/60 |
| 3,123,914 | 3/1964 | De Pietro | 433/60 |
| 4,352,662 | 10/1982 | Lee | 433/56 |

Primary Examiner—Robert P. Swiatek
Attorney, Agent, or Firm—Wm. R. Price

[57] ABSTRACT

A dental articulator, having a spatially oriented mounting table permanently bonded to the one frame, allows for the positioning of mounting plates on the upper and lower frames of an articulator. The first mounting plate is oriented exactly the same on the same frame of each articulator. The mounting plate table, capable of orienting the second mounting plate within a range of positions, is fixed both vertically and horizontally by means of a special mounting block. Therefore, the mounting plate table being fixed, mounted dental casts on the mounting plates may be transferred from one articulator to the other without introduction of vertical or horizontal errors. As a result the relationship of the upper mounting plate to the hinge axis will be the same for each articulator. Additionally, the vertical and horizontal relationship of the lower mounting plate to the upper mounting plate will be the same. This then allows reproducible dental casts which can be transferred from one articulator to another so long as the articulators are manufactured in the same way.

14 Claims, 13 Drawing Figures

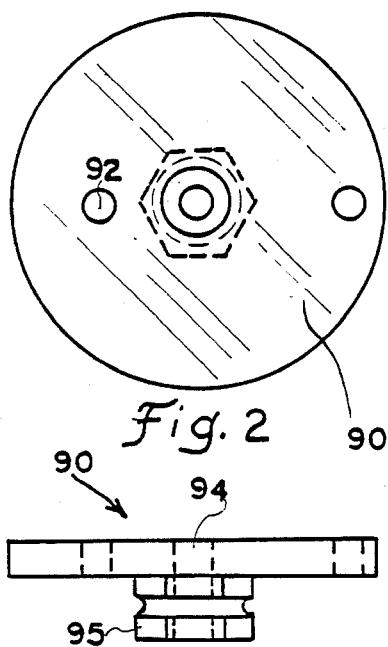
Fig. 2
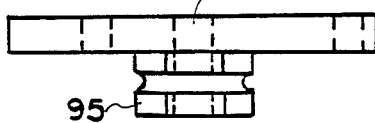
Fig. 3
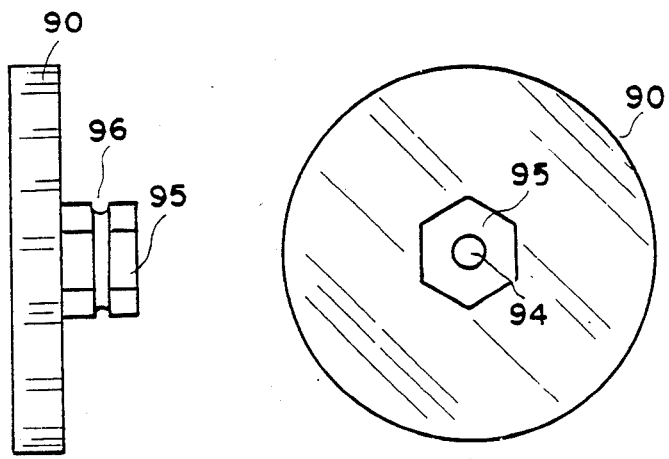
Fig. 4   Fig. 5
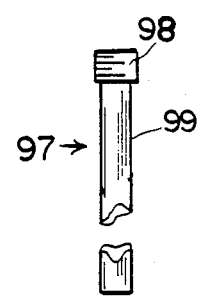
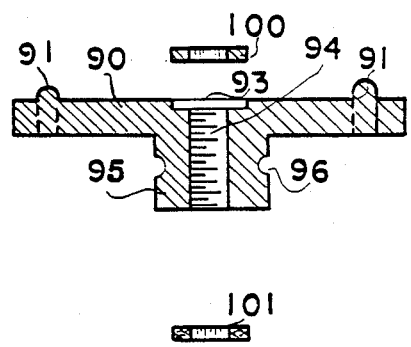
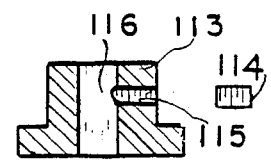
Fig. 6

DENTAL ARTICULATOR WITH SPATIALLY ORIENTED MOUNTING TABLE

FIELD OF THE INVENTION

This invention relates to dental articulators for the mounting of dental restorations in opposed relation, one to the other. This invention relates to dental articulators having an upper and lower frame hinged together so as to simulate the movement of the mandible relative to the maxilla so as to allow for faithful reproduction of dental restorations.

DESCRIPTION OF THE PRIOR ART

Modern dentistry owes a great debt to pioneers in the development of dental articulators. These pioneers include Dr. William Bonwell, Dr. Alfred Gysi, Dr. George Monson, Rudolph Hanau, Dr. Frank Wadsworth and Dr. Charles E. Stuart. As a result, many dental articulators have been proposed through the years which simulate the mandibular condylar joint for mounting upper and lower frame together so as to simulate the movement of the mandible relative to the maxilla. One of the pioneers in this field, Charles E. Stuart, in his U.S. Pat. No. 3,224,096, has developed an articulator which remains in use today. However, due to the simulated mandibular condylar joint, there is sufficient play so that a dental cast mounted on one articulator cannot be moved to another articulator with reproducible results. This problem has been approached by some workers in the art, namely Niles F. Guichet, in U.S. Pat. No. 3,750,289, who proposed a method of checking the centric occlusion of the frame members after a period of use and resetting same if the articulator, for one reason or another, was out of centric alignment.

SUMMARY OF THE INVENTION

According to this invention, however, it is not necessary to check the articulator after a period of use for irregularities in centric alignment, if the articulator is sturdily designed and manufactured correctly in the first instance. According to this invention, the articulator is fabricated according to the following premises:
1. that the mounting plate in each instance is oriented exactly the same on one of the frames of each articulator;
2. that a mounting plate table capable of orienting a second mounting plate within a range of positions is precisely fixed on the other frame;
3. that said mounting plate table is set by means of a mounting block capable of fixing the spatial relationship of the upper and lower mounting plates, in precise vertical and horizontal relation.

As a result, each articulator manufactured in this method has the same relationship of upper mounting plate to hinge axis and the same vertical and horizontal relationship of one mounting plate to the other mounting plate.

BRIEF DESCRIPTION OF THE DRAWINGS

Referring now to the drawings:

FIG. 2 is a plan view of the mounting table of this invention.

FIG. 3 is a side elevation of the mounting table showing the central bore in phantom lines and the mounting guide pin holes in phantom lines.

FIG. 4 is another side elevation of the mounting table without phantom lines.

FIG. 5 is a view of the mounting table from the bottom.

FIG. 6 is an exploded sectional view of the mounting table assembly.

DESCRIPTION OF THE PREFERRED EMBODIMENT

Figure 1:
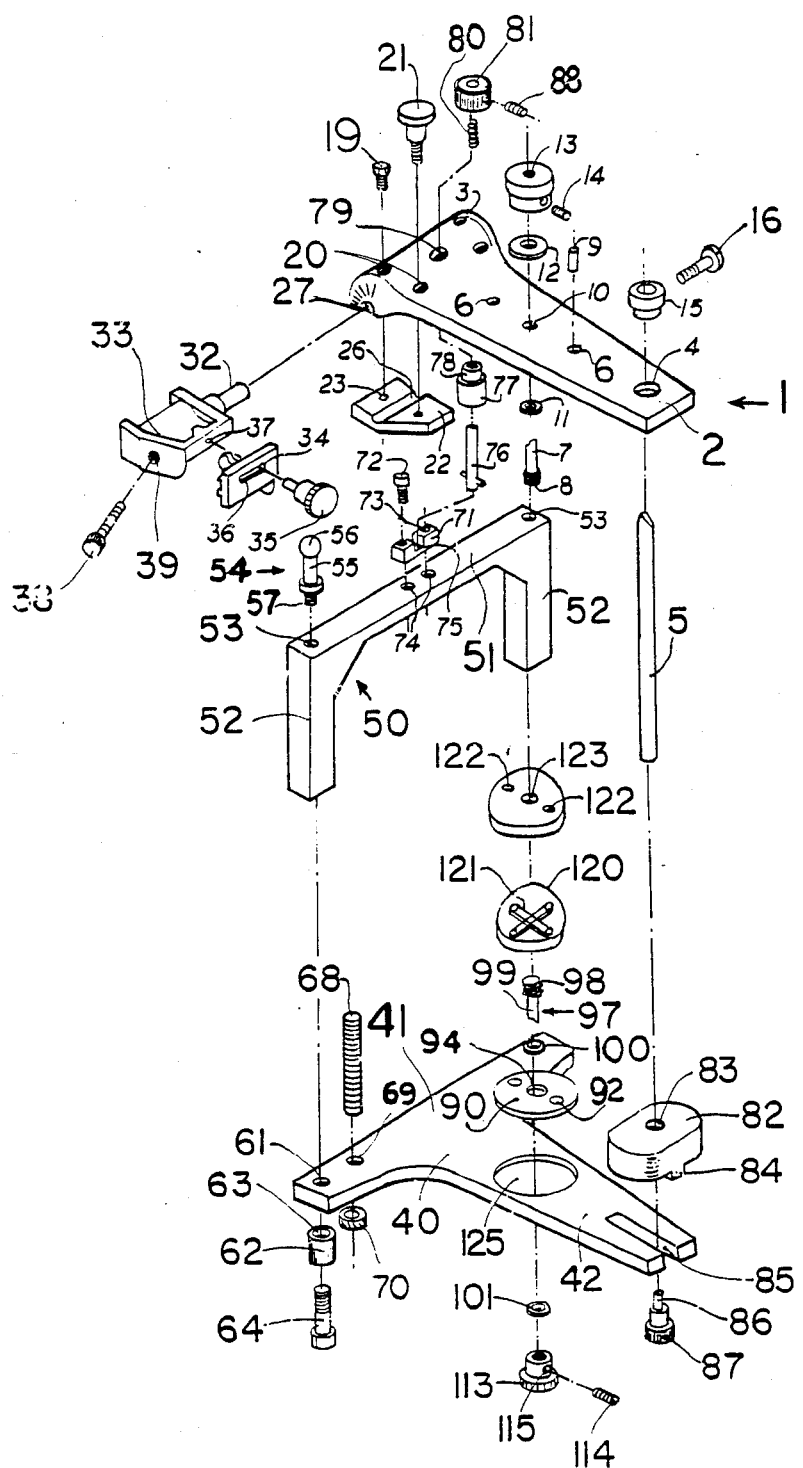
FIG. 1 is an exploded view of the articulator showing the parts in projection.

Essentially all the parts of the finished articulator are shown in the exploded view of FIG. 1. The articulator consists of an upper T-shaped frame 1 having a projecting leg member 2 and a cross piece member 3. An incisal boss hole 4 is provided for the incisal guide pin 5 and a hole 6 for the mounting plate guide pins 9 are illustrated. Hole 10 is provided in about the mid-portion of the projecting leg member 2 for the mounting plate screw 7 having an unthreaded shank and a threaded end 8. The unthreaded portion of the shank, when assembled will project through steel washer 11 through hole 10 and through fiber washer 12 and through the bore of mounting plate knob 13. The shank is then secured into place by provision of set screw 14. In the same method the incisal guide pin 5 can be set when it is placed through the bore of the incisal guide pin boss 15 and locked into position by incisal guide set screw 16. Holes 20 are located in the cross piece 3 of the upper T-shaped frame for provision of the condylar clamp screw 19 and condylar clamp locking screw 21. A condylar guide pin 32 fits into the upper semi-circular groove 27 of the cross piece of the frame member and cooperates with the lower semi-circular groove 26 of condylar guide clamp 22. The condylar clamp locking screw fits into the hole 23 of the condylar guide clamp to secure the condylar guide pin into position. The condylar guide shift member 34 is locked onto the condylar guide member by means of condylar side shift member clamping screw 35 projecting through slot 36 of the condylar guide fossa 33 and locking into hole 37 of the condylar side shift member 34. Condylar locking screw 38 fits into hole 39 in the side of condylar fossa 33. The lower T-shaped frame 40 consists of a cross piece 41 and projecting leg member 42. The C-shaped frame 50, comprising cross portion 51 and leg portion 52, contains a threaded hole 53 for each of the condyle elements 54. The condyle element 54 consists of shank 55, round condyle member 56 and a threaded end 57 which fits into the threaded hole 53. It is thus seen that the condyle element fits into the condylar guide fossa 33 and is moved laterally for lateral condyle shift by the condylar guide shift member 34. The end of the leg portion 52 contains a threaded hole (not shown) for the provision of foot screw 64 which fits through the cylindrical foot member 62 and extends through hole 61 of the cross portion member 41 of the frame to engage with the leg members 52 on either side. An elevating screw 68 projects through hole 69 of the cross portion 41 of the frame and is held into position by lock nut 70. A centering block 71 contains holes 73 for provision of set screws 72 which fit into tapped holes 74 of the cross piece 51 of the C-shaped frame member 50. The centering block 71 has a central detent portion 75 for provision of the end of centering pin assembly 76. Centering pin assembly 76 projects through the bore 78 of centering pin holder 77. The upper part of centering pin holder 77 is of reduced diameter so as to pressure fit into hole 79 of upper frame 1. The upper end of centering pin assembly extends through spring 80 and into the bore of centering pin knob 81. Set screw 88 holds the centering pin 76 in place.

Figure 7:
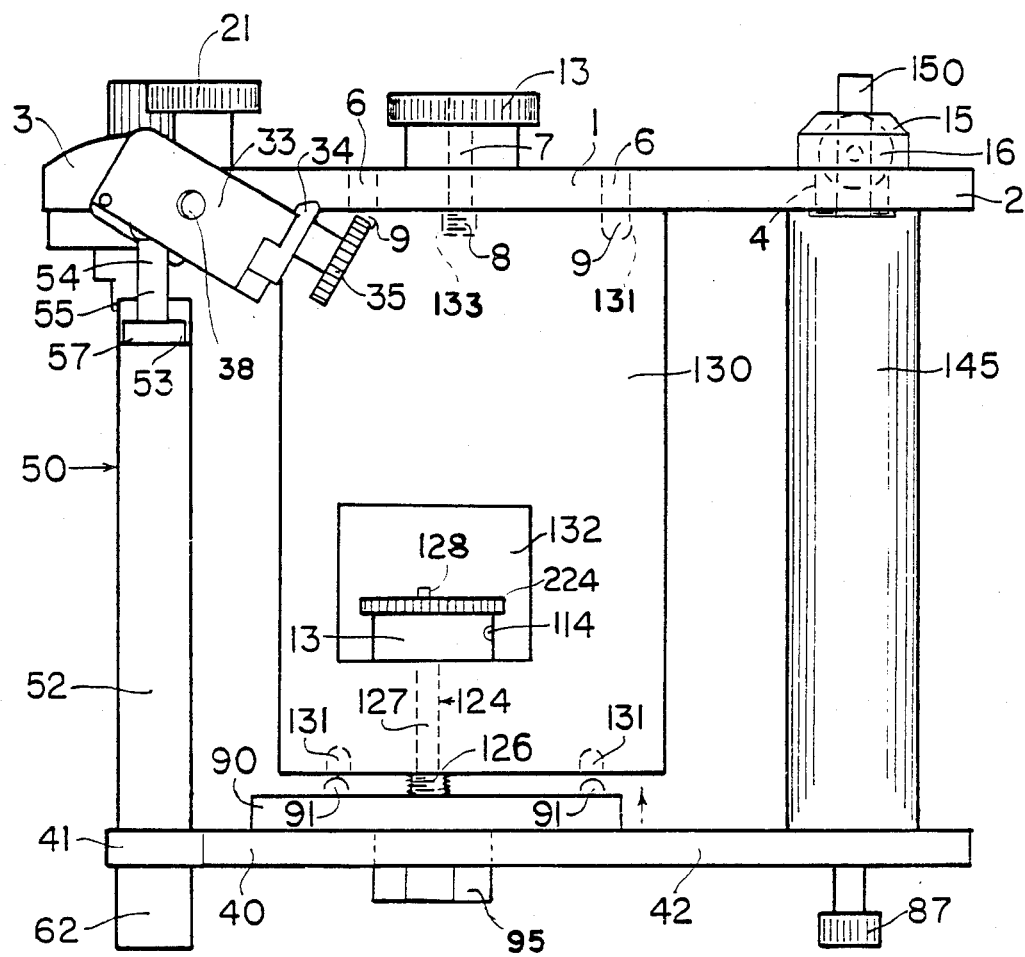
FIG. 7 is a side elevation of the articulator illustrating the mounting block and the incisal mounting gauge pin in use in installing the mounting table.
Figure 8:
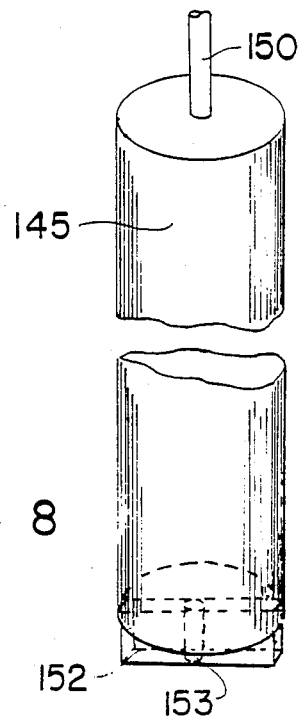
FIG. 8 is a view, in perspective, of the incisal mounting gauge pin.
Figure 9:
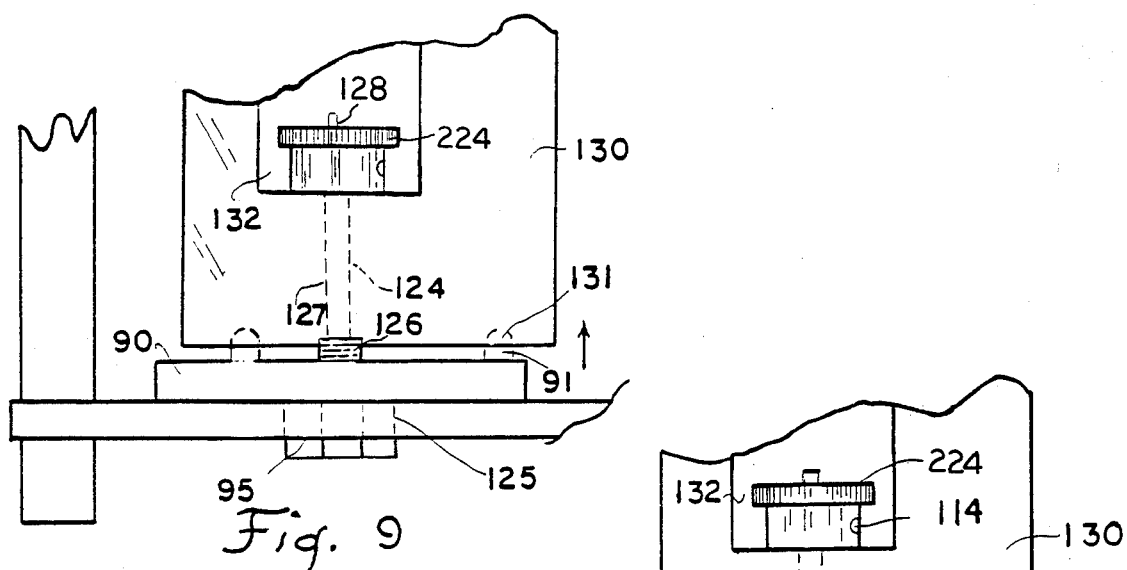
FIG. 9 is an exploded fragmentary view, partially in section, illustrating the relationship of the mounting block to the mounting table.
Figure 10:
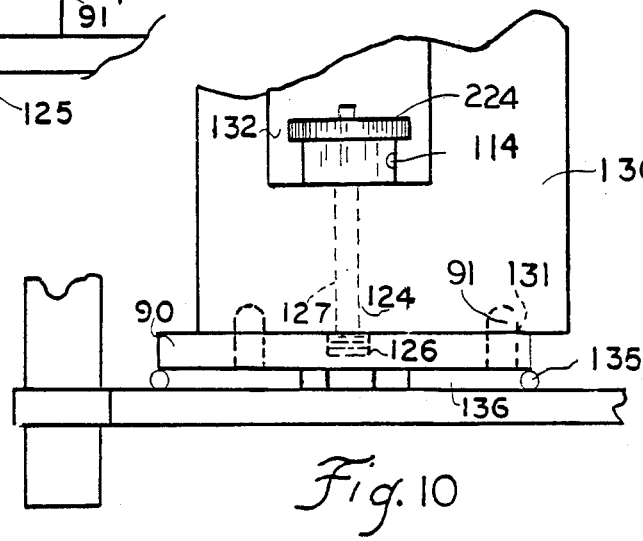
FIG. 10 is an exploded fragmentary view, illustrating the mounting table tightly secured to the mounting block and the relationship of the damming material to it and to the lower frame.

The plastic incisal pin block 82 contains a bore 83 extending completely through its body and through the rectangular incisal guide means 84 adapted to slide into anchoring engagement with the incisal guide means slot 85. It is thus attached to the lower portion of the projecting leg 42 of the frame 40 by means of the manipulation of the knob 87 for the threaded screw 86 in engagement with the threaded bore 83 of the incisal pin block. The mounting table 90, illustrated in detail in FIGS. 2 through 6, contains bores 92 for the insertion of mounting plate guide pins 91 which are pressure fit therein. The planar surface of the mounting table is interrupted by a circular recess 93 for provision of a washer surrounding the central threaded bore 94 which extends through the planar surface through the hexagonal boss 95 to the bottom. The hexagonal boss contains a key way 96 for locking of the potting material to the lower frame as will be described hereinafter. In any event, the mounting plate screw 97, containing a threaded end 98 and the shank portion 99, extends through the steel washer 100 fitted into recess 93 of the mounting table 90 and through the central bore 94. The shank 99 extends through the fiber washer 101 and through the smooth bore of the mounting plate screw knob 113. A threaded bore 115 is provided in the side of the screw knob 113 for provision of the set screw 114. As previously stated, the bore 116 of the mounting plate screw knob 113 is smooth and without threads. The mounting plates 120 are of typical design having a mounting plate surface 121, a threaded bore 123 and mounting pin recesses 122 for provision of the mounting plate guide pins 91. Referring now to FIGS. 7 through 12, there is a hole 125 provided in the projecting leg 42 of the lower frame 40 for provision of the hexagonal boss of the mounting table. The proper placement of the mounting table for planar and vertical separation from the upper mounting plate, fitted onto the upper mounting frame, is provided by means of a mounting block 130 and an incisal mounting gauge pin 150. Referring now to FIGS. 7 and 8, the mounting block has a central opening 132 and has mounting pin recesses 131 at both its top and bottom surfaces. Additionally, the mounting block contains a threaded bore at the top surface for provision of the threaded end 8 of the mounting plate screw 7. Therefore, by manipulation of the mounting plate knob, the threaded end 8 of the mounting plate screw 7 engages with the bore 133 of the mounting block and pulls the mounting block into tight engagement with the surface of the projecting leg member 2 of the upper frame and allows the mounting plate guide pins 9 to engage with the mounting pin recesses 131 of the mounting block.

It will be noted, however, that the mounting table has mounting plate guide pins 91 which are not in engagement with the mounting pin recesses 131 of the mounting block. The mounting plate screw 124 is placed so that its threaded end 126 extends below the mounting block 130, with the shank portion 127 extending upwardly into the central opening 132 of the mounting block so that the mounting plate screw knob 224 can be secured by means of the mounting plate screw 114 onto the flattened shank portion 128 of the shank of the mounting plate set screw. Therefore, by manipulation of the knob 224, the threaded portion 126 of the mounting plate screw 124 can be engaged with the threaded bore 94 of the mounting table. This will allow the mounting table to be pulled upwardly into tight engagement with the lower surface of the mounting plate and allows the mounting plate table guide pins 91 to engage with the mounting plate guide pin recesses 131 of the mounting block, as is clearly shown in FIG. 10.

Figure 11:
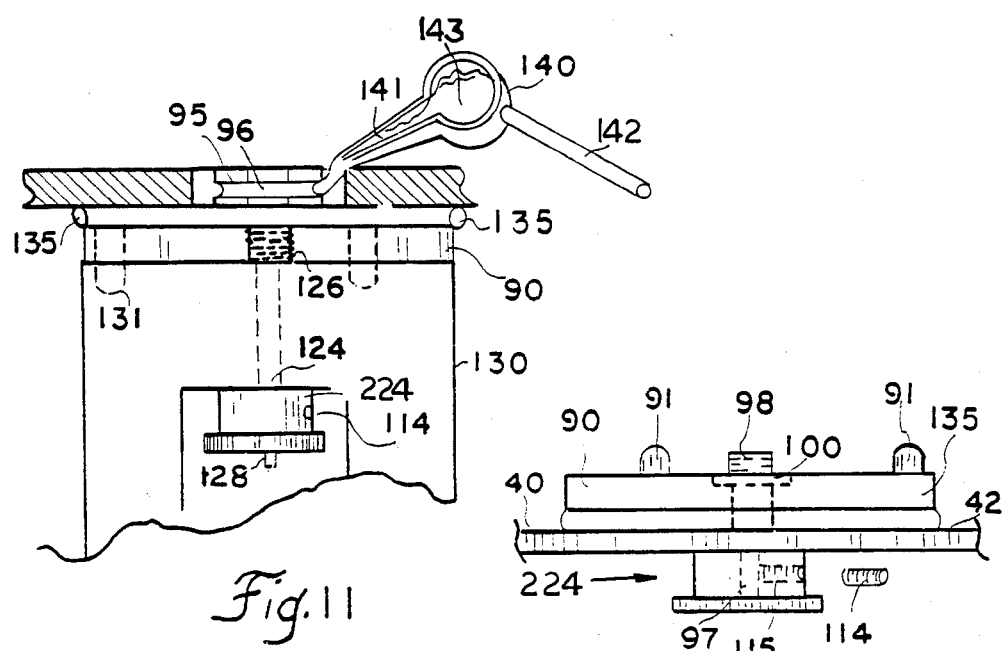
FIG. 11 is an exploded fragmentary view, partially in section, illustrating the lower frame of the articulator inverted so as to allow the introduction of molten potting material to bond the mounting table to said lower frame.
Figure 12:
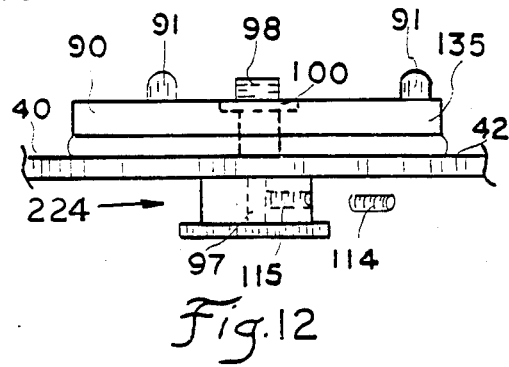
FIG. 12 is a fragmentary view of the mounting table permanently bonded to the lower frame and illustrates the introduction of the mounting plate screw knob onto the shank of the mounting plate screw.
Figure 13:
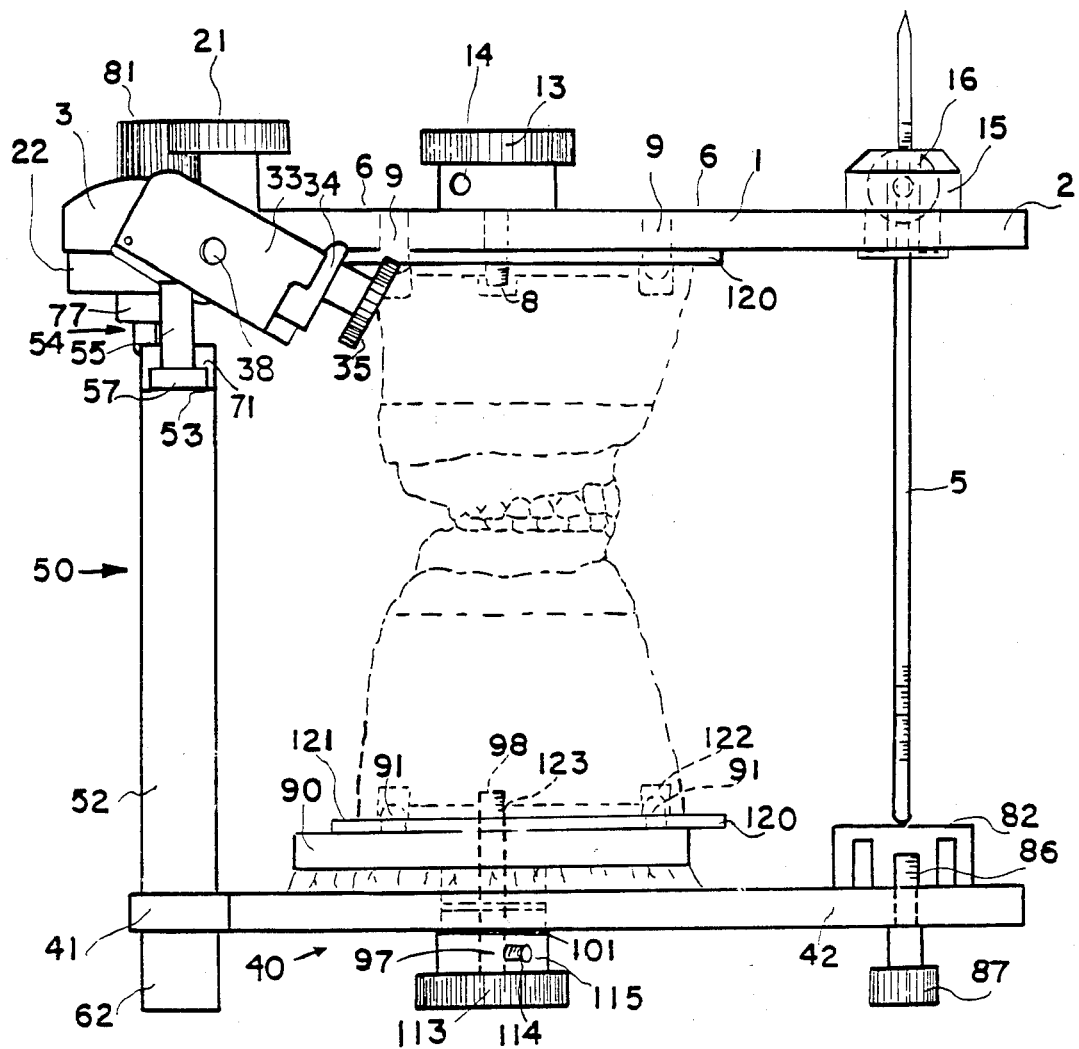
FIG. 13 illustrates the finished articulator with dental casts shown in phantom lines on the mounting plates.

At this point, there is a space between the lower surface of the mounting table 90 and the projecting leg 42 of the frame member 40. A clay-like damming material 135 is thus placed in the space between the periphery of the lower surface of the mounting table 90 and the projecting leg member 42 of the frame, forming a cavity 136. The articulator is then inverted, as is shown in FIG. 11, and a molten potting material 143, contained in the metal pot 140 having a handle 142, is poured through spout 141 into the cavity 136 defined by the damming material 135 on its outer periphery by the hexagonal boss on its inner surface and by the lower surface of the mounting table and the outer circumference of the hole 125 in the projecting leg 42.

As the potting material is allowed to set, the mounting table is then in perfect vertical and horizontal planar relation with the upper frame and the mounting plate guides extending therefrom so that a mounting plate, mounted upon the upper frame member by means of the mounting guide pins 9 and the mounting plate screws 7, will be in perfect alignment with a mounting plate 120 mounted upon the mounting plate 90 so that the mounting guide pins 91 are in perfect alignment with the mounting pin recesses 122 of the mounting guide plate 120.

Once the potting material has set, the set screw 114 can be removed so that the knob 224 can be taken away from the shank portion 128 of the mounting plate screw and the threaded end portion 126 can be disengaged from the threaded bore 94 of the mounting table. The mounting plate screw can then be removed and the mounting block can be completely removed from the articulator.

The mounting gauge pin 145 has a projecting incisal gauge pin 150 which projects through the incisal boss hole 4 and through the bore of the incisal boss 15 where it is secured into position by set screw 16. In the same manner, the rectangular incisal guide means 152 is fitted into the incisal guide slot 86. The rectangular incisal guide means 152 contains a threaded hole 153 for engagement with screw 86. Thus by manipulation of the knurled knob 87, the mounting gauge guide pin can be securely fastened into position.

While the term potting material has been used throughout to refer to a molten alloy, it is possible to utilize other materials which will set up and harden without shrinkage. Such materials may be non-metallic in nature, such as polymeric materials, such as epoxy resins, polyurethanes or acrylic polymers, which may be employed to bond the mounting table 90 to the frame member 40. Various dental alloys with low melting temperatures are suitable due to their ease of handling and their low coefficients of expansion and contraction, and other desirable characteristics.

As previously indicated, once the potting material has set, both mounting block and the mounting gauge pins can be removed, and the mounting plate screw 97 may then be inserted through the steel washer 100 through the bore 94 to project through the bottom of the boss 95. Since the shank 99 of the mounting plate screw is of smaller diameter than the threaded bore of the mounting table bore, this allows for free movement of the mounting plate screw to engage with the threaded bore 123 of the mounting plate so it can be tightly secured onto the mounting table 90. The knob 113 is fitted over the shank 99 of the mounting plate screw 97 and is secured into position by insertion of the set screw 114 into threaded bore 115 which communicates with the central bore 116 of the knob.

It will be apparent to those skilled in the art that it is possible to reverse the procedure so that the mounting table is placed on the upper frame and the mounting plates fastened directly to the lower frame of the articulator. It is important, however, that at the time that the mounting plate is permanently bonded to the frame portion that the two frames are held in precise vertical and planar relation at two points. According to the invention, this is accomplished by use of the incisal mounting gauge pin at the incisal portion of the articulator and by use of the mounting block at the middle portion of the two frames of the articulator.

Many modifications will occur to those skilled in the art from the description hereinabove given and such is meant to be exemplary in nature, except so as to be commensurate in scope with the appended claims.

I claim:

1. A dental articulator for the support of dental casts in opposed relation to each other, including:
   A. an upper frame;
   B. a lower frame;
   C. a joint means, simulating the mandibular condylar joint for mounting said upper and lower frames together at the rear end, for movement in a manner simulating the movement of the mandible relative to the maxilla;
   D. mounting plates for attachment to said frames for mounting of dental casts in opposed relation to each other;
   E. a mounting plate table, having a planar surface on one side and being permanently bonded on the other side to one of said frames at the frame's mid-portion in precise vertical and horizontal planar relation to the other frame for mounting of one of said mounting plates in precise vertical and horizontal planar relation to said other mounting plate;
   1. said precise vertical and horizontal planar relation of said mounting plate table, relative to one frame, having been established by a standard gauge means positioned between the upper and lower frames at both the mid-portion and front of said frames; and
   F. bonding means for permanently securing said mounting plate table to one of said frames in precise vertical and horizontal planar relation to said other frame.

2. A dental articulator, as defined in claim 1, in which each of said mounting plates contains pin recesses on one side and a threaded bore on the other side and in which said mounting plate table contains projecting pins for registry with the pin recesses of one of said mounting plates.

3. A dental articulator, as defined in claim 2, in which said mounting plate table comprises:
   A. a centrally located bore;
   B. a projecting threaded stud having a shank of smaller diameter than said bore; and
   C. a removable knob for detachable connection to the end portion of the shank of said threaded stud for turning of the shank of said threaded stud, so as to engage the threaded bore of one of said mounting plates with said threaded stud.

4. A dental articulator, as defined in claim 1, in which:
   A. said mounting plate table contains a boss projecting from one of its surfaces and a bore extending through said boss and opening on said planar surface of said mounting table; and
   B. said frame member has a large hole in its mid-portion for receipt of said projecting boss prior to being bonded to said mounting table.

5. A dental articulator, as defined in claim 4, in which said bore is threaded.

6. A dental articulator, as defined in claim 4, in which said projecting boss has a key way extending around its periphery.

7. A dental articulator, as defined in claim 4, in which said projecting boss is hexagonal.

8. A dental articulator, as defined in claim 4, which includes:
   A. a projecting threaded stud having a shank of smaller diameter than said bore of said boss; and
   B. a removable knob detachably secured to the end portion of the shank of said threaded stud for turning of said shank of said threaded stud to engage said threaded stud with the threaded bore of said mounting plate.

9. A dental articulator, as defined in claim 8, in which said planar surface of said mounting table contains a recess around the bore of said boss and a washer fitted in said recess so as to allow for effortless turning of said threaded stud.

10. A method of assembling a dental articulator, suitable for the mounting of dental casts in precise and reproducibly opposed alignment, which comprises the steps of mounting an upper frame of an articulator to a lower frame of an articulator, in which:
    A. said upper frame has a forwardly projecting member having laterally extending fossa like condylar guide members;
    B. said lower frame has a forwardly projecting member having laterally located vertically projecting support posts and mandibular condyle elements supported thereon for mounting with the condylar guide members of said upper frame; and C. the improvement which comprises permanently bonding a mounting table onto one of said frames for the placement of mounting plates into said precise and reproducibly vertically opposed relation on the said upper and lower frames, which comprises the steps of:
1. forming a hole in the mid-portion of one of said frames;
2. detachably securing a standardized mounting block at about the mid-point of said frame;
3. detachably securing said mounting table to said mounting block, said mounting table comprising;
    (a) a flat planar surface;
    (b) an oppositely projecting boss having a centrally located threaded bore, said boss projecting from the opposite surface of said mounting table;
D. detachably positioning a standardized gauge pin at the front portion of said upper and lower frame members to vertically separate said frame members into precise alignment;
E. damming up the area between the said frame member and said mounting table with a detachable clay-like material;
F. pouring a molten potting compound through the hole in said frame into the cavity formed by the boss of said mounting table, the dammed up portion and said frame;
G. allowing said potting compound to set so as to permanently bond said mounting table to said frame;
H. removing the clay-like damming material from said frame, mounting table and set potting material;
I. detaching said mounting block from said mounting table; and
J. detaching said gauge pin from said upper and lower frames.

11. A method of assembling a dental articulator, as defined in claim 10, in which:
A. the hole in the mid-portion of said frame is formed in said lower forwardly projecting frame member; and
B. the articulator is inverted prior to the step of pouring the molten potting compound through said hole.

12. A method of assembling a dental articulator, as defined in claim 10, in which the step of detachably securing said mounting table to said mounting block includes:
A. engaging a threaded stud to said mounting block and to the threaded bore of said mounting table; and
B. turning the shaft of said threaded stud, so as to tightly engage said mounting table to the end of said mounting block.

13. A method of assembling a dental articulator, as defined in claim 10, which comprises the further steps of:
A. placing a washer around the bore of said mounting table;
B. inserting the shank end of a threaded stud through the washer and through said bore;
C. placing a knob onto the end portion of the shank end of said threaded stud; and
D. detachably securing said knob onto said shank end of said threaded stud.

14. In a mounting block for use with a mounting bolt having a knob, an elongated unthreaded shank and a threaded end for use in precisely and accurately mounting a mounting plate table in relation to projecting pins of one of a pair of frames of a dental articulator, said mounting plate table having a threaded bore and projecting mounting plate pins, said mounting block comprising:
A. a central body portion;
B. recesses at each end for receiving said projecting mounting pins;
C. a central opening extending through said body portion for reception of the knob and shank of said mounting bolt; and
D. a central bore, at one end of said mounting block, and in communication with said central opening of said mounting block for receiving the shank portion of said mounting bolt and for allowing the free rotation of the shank of said mounting bolt for turnably engaging the threaded end of said mounting bolt with the threaded bore of the mounting plate table.

* * * * *